United States Patent
Thabuis et al.

(10) Patent No.: US 9,629,332 B2
(45) Date of Patent: *Apr. 25, 2017

(54) **RESISTANCE TO *NASONOVIA RIBISNIGRI* BIOTYPE 1 (NR:1) FROM *LACTUCA SERRIOLA***

(71) Applicant: RIJK ZWAAN ZAADTEELT EN ZAADHANDEL B.V., De Lier (NL)

(72) Inventors: Arnaud Paul Pierre Thabuis, Montfavet (FR); Korstiaan Cornelis Teekens, De Lier (NL); Zeger Otto van Herwijnen, Rotterdam (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/467,799

(22) Filed: Aug. 25, 2014

(65) Prior Publication Data

US 2015/0047068 A1    Feb. 12, 2015

Related U.S. Application Data

(63) Continuation of application No. 12/947,727, filed on Nov. 16, 2010, now Pat. No. 8,816,158.

(51) Int. Cl.
*A01H 5/12* (2006.01)
*A23L 19/00* (2016.01)

(52) U.S. Cl.
CPC .............. *A01H 5/12* (2013.01); *A23L 19/00* (2016.08)

(58) Field of Classification Search
None
See application file for complete search history.

(56) References Cited

U.S. PATENT DOCUMENTS 8,816,158 B2 * 8/2014 Thabuis ................ A23L 1/212
435/410
2011/0126308 A1 5/2011 Thabuis et al.

FOREIGN PATENT DOCUMENTS

WO      97/46080     12/1997
WO      2011/058192   5/2011

OTHER PUBLICATIONS

Eenink, A.H. et. al., "Resistance of Lettuce (Lactuca) to the Leaf Aphid Nasonovia Ribis Nigrl Transfer of Resistance from *L. Virosa* to *L. Sativa* by Interspecific Crosses and Selection of Resistant Breeding Lines," Euphytica, vol. 31 p. 291-299 (1982).
Reinink K. et. al., "Comparison of Sources of Resistance to Leaf Aphids in Lettuce," Euphytica, vol. 40, No. 1/02, Jan. 1, 1989, p. 21-29.
"Resistance to the Lettuce Leaf Aphid Nasonovia Ribisnigri." IP.COM Journal, West Henrietta, NY. Nov. 4, 2008.
Anonymous, 2008, Resistance to the lettuce leaf aphid Nasonovia ribisnigri, Disclosure No. IPCOM000176078D, Nov. 4, 2008, IP.com Prior Art Database Disclosure. <http://ip.com/IPCOM/000176078>.

* cited by examiner

*Primary Examiner* — Eileen O Hara
(74) *Attorney, Agent, or Firm* — Vedder Price P.C.; Thomas J. Kowalski; Deborah L. Lu

(57) ABSTRACT

The present invention relates to lettuce (*Lactuca sativa* L.) plants being resistant against the lettuce aphid *Nasonovia ribisnigri* (Mosley). The invention further relates to parts of the plants, in particular to the seeds and to other propagation material, and to progeny of the plants.

9 Claims, No Drawings

RESISTANCE TO *NASONOVIA RIBISNIGRI* BIOTYPE 1 (NR:1) FROM *LACTUCA SERRIOLA*

RELATED APPLICATIONS AND INCORPORATION BY REFERENCE

The present application is a continuation of U.S. patent application Ser. No. 12/947,727 filed on Nov. 16, 2010. Reference is made to the U.S. application Ser. No. 12/947,722 filed Nov. 16, 2010.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to lettuce (*Lactuca sativa* L.) plants being resistant against the lettuce aphid *Nasonovia ribisnigri* (Mosley). The invention further relates to parts of the plants, in particular to the seeds and to other propagation material, and to progeny of the plants.

BACKGROUND

The lettuce aphid (*Nasonovia ribisnigri* (Mosley) is a major pest occurring in lettuce worldwide. The problem started to be severe for lettuce production in the 1970's in North Western Europe and spread rapidly all across Europe. In the 1980's, the aphid was detected in Canada. Later on, the problem was reported in the USA (California and Arizona). More recently, the lettuce aphid was found in New Zealand and Australia.

Lettuce aphids can colonize lettuce plants at any plant stage and feed preferably from younger leaves. Large amount of aphids on the plant are able to reduce plant growth and deform the shape of the head so that the lettuce heads are then not marketable. The presence of high amount of aphids in lettuce heads is a reason for retailers to refuse to buy lettuce from growers. At young plant stage, it is possible to control the lettuce aphid using insecticide. Several products were reported efficient to control aphid population. However, resistance to chemicals were reported in some aphid population. Moreover, at maturity, it is not possible to control aphid using insecticide because the chemical product cannot enter the lettuce head.

One of the most valuable strategies to control lettuce aphids is the genetic resistance. Extensive genebank screening was performed and some *Lactuca virosa* accessions were found completely resistant to *Nasonovia ribisnigri*. However, *Lactuca virosa* is in the second gene pool of the Lactuca germplasm according to the definition of Harlan. Therefore, these interspecific crosses are sterile, and the use of bridge species (as *Lactuca serriola*) was necessary to transfer the resistance into *L. sativa*. Genetic analyses showed that the resistance to *Nasonovia ribisnigri* was controlled by a single dominant gene (Nr gene) in a *Lactuca sativa* background.

However, breeders experienced that the release of varieties resistant to lettuce aphid was not straightforward. The Nr-resistance gene was found tightly linked to recessive genes conferring strong pleiotropic effect. Such plants showed a reduced growth, a pale green colour and a lack of fertility in seed set. Using large-sized progeny and molecular markers enabled Rijk Zwaan lettuce breeders to find resistant recombinant plants without the negative side-effect phenotype.

After this finding, the release of varieties resistant to *Nasonovia* became more and more important. The resistance trait became a major requirement for outdoor lettuce production for the processing industry and also for the fresh market. More recently, partial resistance to *Nasonovia* was reported in one *L. serriola* accession PI 491093 (Mc Creight, 2008)

In 2007, populations of lettuce aphids able to infect varieties resistant to *Nasonovia ribisnigri* were found in 4 distinct areas in Europe (France, Germany, Belgium and Austria). Four isolates (2 from France and 2 from Germany) were analysed further by Naktuinbouw (Netherlands Inspection Service for Horticulture) and they concluded the existence of a new *Nasonovia ribisnigri* biotype. This biotype is officially named Nr:1 and is able to overcome the Nr resistance gene. Nr:0 biotype can still be efficiently controlled by the Nr gene. Naktuinbouw also reported that IVT 280, the original source of the Nr:0 resistance, was susceptible in their tests.

After the breakthrough of the Nr gene by the Nr:1 biotype in practice, there was a need to find a resistance to the Nr:1 biotype.

Citation or identification of any document in this application is not an admission that such document is available as prior art to the present invention.

SUMMARY OF THE INVENTION

In the research leading to the present invention new lettuce plants were developed which are resistant against Nr:1. The resistance was surprisingly found in *Lactuca serriola*. *L. serriola* was never reported being resistant to *Nasonovia ribisnigri*.

The present invention thus provides a lettuce (*Lactuca sativa* L.) plant, which has the Nr:1 resistance as found in plants grown from seeds of seedlot 10G.913569 representative seeds of which were deposited on 29 Sep. 2010 with NCIMB Ltd, Ferguson Building, Craibstone Estate, Bucksburn, Aberdeen AB21 9YA, UK under deposit accession number NCIMB 41763.

The invention also relates to the use of *L. serriola* as a source of resistance against *Nasonovia ribisnigri* biotype 1 (Nr:1). The source of resistance is suitably introduced in susceptible lettuce plants (*L. sativa*) by introgression.

The invention further relates to *Lactuca sativa* plants that are resistant against *Nasonovia ribisnigri* biotype 1 (Nr:1), obtainable by crossing a *L. serriola* plant with a *Lactuca sativa* plant.

According to a further aspect thereof, the invention provides progeny of the plant as claimed, seeds of the plant as claimed and parts of the plant as claimed.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposits

The Deposits with NCIMB Ltd, Ferguson Building, Craibstone Estate, Bucksburn, Aberdeen AB21 9YA, UK, under deposit accession number NCIMB 41763 was made pursuant to the terms of the Budapest Treaty. Upon issuance of a patent, all restrictions upon the deposit will be removed, and the deposit is intended to meet the requirements of 37 CFR. §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

In one embodiment, the invention relates to a lettuce plant resistant against Nr:1, wherein said resistance is obtainable by introgression from a plant of which representative seed was deposited with the NCIMB under accession number NCIMB 41763.

In one embodiment, the invention relates to a lettuce plant resistant against Nr:1, wherein said trait is introgressed from a plant of which representative seed was deposited with the NCIMB under accession number NCIMB 41763. "Introgression" as used herein is intended to mean introduction of a Nr:1 resistance into a plant not carrying the Nr:1 resistance by means of crossing and selection. Introgression is not limited to one cross only but encompasses the minimum number of generations needed for the plant to become resistant, preferably stably resistant.

In one embodiment the invention relates to a lettuce plant resistant against Nr:1, obtainable by crossing a lettuce plant susceptible to Nr:1 with a plant of which representative seeds was deposited with the NCIMB under NCIMB accession number 41763 and selecting preferably in the F2 progeny of the cross for plants being resistant against *Nasonovia ribisingi* biotype 1 (Nr:1).

In one embodiment, the invention relates to a lettuce plant resistant against Nr:1, which plant is obtainable by crossing a lettuce plant with a plant grown from seedlot 10G.913569 representative seeds of which were deposited with the NCIMB under NCIMB accession number 41763 and selecting in the F2 progeny of the cross, which is obtained after selfing the F1, for plants being resistant against *Nasonovia ribisingi* biotype 1 (Nr:1).

The resistance trait as present in the deposited material is transferred in a pattern consistent with recessive inheritance, and selection is thus suitably made in the second generation (F2) after having selfed the F1.

In one embodiment, the invention further relates to a lettuce plant resistant against Nr:1, wherein when said plant is homozygous for said trait and said plant homozygous for said trait is crossed with a tester plant homozygous for the said trait, plants of the first generation progeny resulting from said cross show a 1:0 segregation for resistance against Nr:1.

In one embodiment, when said plants of said first generation progeny are self-pollinated, plants of the resulting second generation progeny show a 1:0 segregation for resistance against Nr:1. In one embodiment, the tester plant is a lettuce plant grown from seeds deposited with the NCIMB under NCIMB accession number 41763.

In one embodiment, the tester plant is a plant grown from seeds deposited with the NCIMB under NCIMB accession number 41763, or a progeny of said plant which is resistant against Nr:1.

In one embodiment, the lettuce plants of the invention do essentially not show any negative pleiotropic effects.

The invention further relates to seed of the lettuce plants of the invention and to other parts of the plant that are suitable for sexual reproduction, i.e. propagation material. Such parts are for example selected from the group consisting of microspores, pollen, ovaries, ovules, embryo sacs and egg cells.

In addition, the invention relates to parts of the plant that are suitable for vegetative reproduction, in particular cuttings, roots, stems, cells, protoplasts, and tissue culture of the lettuce plants of the invention. The tissue culture comprises regenerable cells. Such a tissue culture can be derived from leaves, pollen, embryos, cotyledon, hypocotyls, meristematic cells, roots, root tips, anthers, flowers, seeds and stems.

The invention also relates to progeny of the lettuce plants of the invention. Such progeny can be produced by sexual or vegetative reproduction of a plant of the invention or a progeny plant thereof.

The regenerated progeny plants have the same genetic basis for resistance against Nr:1 as the plant of which representative seed was deposited under NCIMB accession number NCIMB 41763. This means that in case the genetic basis is homozygous such progeny has the same characteristics as claimed for the lettuce plants of the invention. In case the genetic basis is present in heterozygous form, the progeny does not show resistance against Nr:1 as is present in the plant of the invention, but still contains the alleles responsible for the Nr:1 resistance, and is therefore still a source for Nr:1 resistance.

In addition to this, the plant may be modified in one or more other characteristics. Such additional modifications are for example effected by mutagenesis or by transformation with a transgene. Alternatively, modifications in characteristics other than the Nr:1 resistance can be introduced by introducing the Nr:1 resistance in a different background. In the first case the resistant plant is taken as the original plant and modified. In the latter case the resistance is transferred to another plant, in particular a susceptible plant.

As used herein the word "progeny" is intended to mean the offspring or the first and all further descendants from a cross with a plant of the invention that is Nr:1 resistant.

Progeny of the invention are descendants of any cross with a plant of the invention that carries the Nr:1 resistance. Progeny plants are preferably also resistant.

"Progeny" also encompasses plants that carry the Nr:1 resistance of the invention which are obtained from other plants of the invention by vegetative propagation or multiplication.

In one embodiment, the invention relates to lettuce plants that carry the trait of the invention, being resistant against Nr:1, and having acquired said trait by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the genetic information is acquired is formed by plants grown from the deposited seeds or sexual or vegetative descendants therefrom.

The invention, furthermore, relates to hybrid seed and to a method of producing hybrid seed comprising crossing a first parent plant with a second parent plant and harvesting the resultant hybrid seed. In order for the hybrid seed to express the Nr:1 resistance of the invention, at least one of the parent plants need to be homozygous for the Nr:1 resistance but is not necessarily uniform for other characteristics.

The invention also relates to the germplasm of plants of the invention. The germplasm is constituted by all inherited characteristics of an organism and according to the invention encompasses at least the trait of the invention, being the resistance against Nr:1.

The invention further relates to cells of the lettuce plants are resistant against Nr:1. Each cell of such lettuce plants carries the genetic information that leads to phenotypic expression of said trait. The cell may be an individual cell or be part of a lettuce plant or lettuce plant part.

The invention further relates to the head of a lettuce plant as claimed. The invention further relates to a food product, comprising the lettuce head or parts thereof. In particular, the food product comprises leaves of the lettuce plant or parts thereof. The food product is for example a salad or a salad mixture comprising leaves of the lettuce plant of the invention.

In this specification the term "Nr:1 resistance" is intended to mean having the genetic information (in particular a gene, genes, locus, loci, allele or alleles) that in homozygous state leads to the plant no longer being susceptible to *Nasonovia ribisnigri* biotype 1 (Nr:1) and which resistance is as found in plants of which representative seeds were deposited under accession number NCIMB 41763, in particular in plants grown from the deposited seeds.

Selection of plants for breeding therefore can also be independent of the phenotype of a plant and instead can be based on genetic investigations. For example, one can utilize a suitable genetic marker which is closely genetically linked to a trait of interest—the Nr:1 resistance trait in this instance, e.g., as identified using seed deposited under deposit accession number NCIMB 41763. These markers can be used to identify the presence of the trait in the offspring of a particular cross (e.g., two heterozygous plants that carry the genetic information for the Nr:1 resistance trait but do not have that phenotype because it is recessive and they are not homozygous therefor), and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Methods for marker assisted selection are of particular utility in the case of recessive traits and variable phenotypes, or where conventional assays may be more expensive, time consuming or otherwise disadvantageous, and types of genetic markers which could be used in accordance with the invention include, but are not necessarily limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs). Reference is made to U.S. Pat. No. 7,705,206, for documents and a discussion relating to the foregoing methods; and, U.S. Pat. No. 7,705,206, and the documents cited therein, including as to the foregoing methods, are hereby incorporated herein by reference consistent with the above RELATED APPLICATIONS & INCORPORATION BY REFERENCE section.

In an embodiment this genetic information is substantially identical to the genetic information that encodes the Nr:1 resistance trait as found in plants of which representative seeds were deposited under deposit accession number NCIMB 41763, in particular plants grown from seeds as deposited under deposit accession number NCIMB 41763 (wherein "substantially identical" is identical to the genetic information in the seeds deposited under NCIMB 41763, or so similar to the genetic information in the seeds deposited under NCIMB 41763 at the locus or gene that gives rise to expression of the Nr:1 resistance trait phenotype in the seeds deposited under deposit number NCIMB 41763 such that the sample also has the Nr:1 resistance trait, e.g., a sample can be "substantially identical" in its genome to seeds deposited under deposit number NCIMB 41763 because it is different than the genome of seeds deposited under deposit numbers NCIMB 41763 due to the degeneracy of the genetic code).

In an embodiment, the invention thus relates to a plant, showing the Nr:1 resistance trait, which plant is obtainable by:
 a) growing plants representative seed of which was deposited under NCIMB 41763;
 b) crossing a plant from step a) with a plant that does not have the Nr:1 resistance trait to obtain an F1 population;
 c) selfing plants from the F1 to obtain a F2 population; and
 d) identifying plants showing the Nr:1 resistance trait in the F2 population as lettuce plant resistant against Nr:1.

In the method described above steps c) and d) can be repeated one or more times by selfing an Fn population to obtain an Fn+1 population and identifying plants showing the Nr:1 resistance trait in the Fn+1 population as lettuce plant resistant against Nr:1.

The genotype as far as it concerns the Nr:1 resistance trait is the same as or substantially similar or identical to genotype as found in the deposited seeds. On a nucleic acid molecule basis, this can mean a first nucleic acid molecule having at least about 95, 96, 97, 98 or 99 percent identity with a second nucleic molecule, wherein the second nucleic acid molecule is of a herein identified or exemplified or deposited plant, plant part, seed, cell or the like, and the expression of both the first and second nucleic acid molecules in a plant results in the phenotype of the Nr:1 resistance trait. The part of the genotype of a plant that causes the Nr:1 resistance trait will be called herein the "genetic information that encodes the Nr:1 resistance trait". Presence of this genetic information is phenotypically visible and plants having this genetic information can thus be selected on the basis of this phenotypic expression of the underlying gene or genes.

As used herein "genetic information" is intended to mean the portion of the genome, e.g. gene or genes, that are responsible for the formation of significantly more leaves; which portion of the genome can be detected in the genome, e.g. by detecting polymorphisms in the genome of "Nr:1 resistance trait" plants of which representative seed was deposited under deposit accession number NCIMB 41763, and that portion of the genome, particularly the portion that gives rise to expression of the "Nr:1 resistance trait" can thus be isolated from the genome and can be an isolated nucleic acid molecule encoding the Nr:1 resistance trait (which when introduced into the genome of a regenerable cell of a plant that does not carry this genotype and when in the cell operably linked to and under the control of a suitable promoter, gives rise to the expression of the "Nr:1 resistance trait" in a plant regenerated from a tissue culture of such regenerable cells into which the isolated nucleic acid molecule has been introduced and is present in the cells operably linked to and under the control of a suitable promoter).

The presence of the genetic information that is responsible for the Nr:1 resistance trait of the invention in the genome of a plant that shows a Nr:1 resistant characteristic can be determined with the following test: The plant to be tested should be or should be made to be homozygous for the genetic information responsible for the Nr:1 resistance trait. The skilled person knows how to obtain a plant that is homozygous for the trait to be tested, e.g., via selfing or self mating or self crossing. This homozygous plant is then crossed with a tester plant that carries the genetic information that is responsible for the trait of the invention in homozygous condition. If the plant to be tested has a Nr:1 resistant characteristic as a result of the same genetic information that is responsible for the trait of the invention, all progeny plants of this first cross and successive generations will express the trait. If the Nr:1 resistant characteristic of the plant to be tested is the result of a different part of the genome, e.g. another gene or locus, segregation will occur. The tester plant can be any plant that carries the genetic information of the invention in homozygous condition, such as plants of which representative seed was deposited under accession number NCIMB 41763 or plants directly grown from the deposited seeds or progeny thereof that has retained the trait.

In an embodiment of the invention a plant is provided that comprises the Nr:1 resistance trait and thus when crossed with a tester plant, that comprises the Nr:1 resistance trait of the invention and representative seed of which as deposited with the NCIMB under accession numbers NCIMB 41763, or a progeny plant thereof that comprises the Nr:1 resistance trait comprised in plants representative seed of which was deposited with the NCIMB under accession number NCIMB 41763 or a plant derived therefrom and comprising the Nr:1 resistance trait, plants of the first generation progeny (F1) of said cross show a 1:0 segregation for the Nr:1 resistance trait. In both the tester plant and the plant of the invention the Nr:1 resistance trait is present in homozygous condition. Plants of the second and further generations, if obtained by selfing also show a 1:0 segregation for the Nr:1 resistance trait. The tester plant can be a plant of which representative seed was deposited with the NCIMB under accession number NCIMB 41763. When the genetic information responsible for the Nr:1 resistance trait as contained in the deposit is present in a plant, the plant is a plant of the invention (and seeds therefrom are seeds of the invention, plant parts thereof are plant parts of the invention, etc.).

The Nr:1 resistant characteristic of the invention has a genetic basis in the genome of the plant. With the above described cross with a tester plant, plants can be identified as being plants of the invention.

The Nr:1 resistance trait is independent of other traits of a plant. The trait can thus occur in plants that are completely different in all their other characteristics, for example in different varieties.

The deposited seeds contain in their genome the genetic information that encodes the Nr:1 resistance trait. The deposited seeds are thus a source for the genetic information that leads to the trait. The skilled person is capable of introducing the trait into any other plant he desires. A plant resulting from the initial cross between a first parent plant with a second parent plant that contains the genetic information responsible for the Nr:1 resistance trait, cannot yet be identified as being a plant of the invention. Therefore, an F2 generation is produced by selfing plants of the F1 and assessing the number of leaves of the F2 progeny plant and comparing it with the number of leaves of the first parent plant. If this number is at least 1.25 times higher than the number of leaves in the first parent plant, the progeny plant is a plant of the invention.

In one embodiment, the source from which the genetic information is acquired is formed by plants grown from the deposited seeds or sexual or vegetative descendants therefrom.

It is clear, however, that a parent that provides the trait of the invention is not necessarily a plant grown directly from the deposited seeds. For example, the parent can also be a progeny plant from the seed or a progeny plant from seeds that are identified to have or to have acquired the trait of the invention by other means.

In an embodiment, the invention relates to plants that carry the trait of the invention and have acquired said trait by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that can be introduced by backcrossing, useful traits can be introduced directly into a Nr:1 resistance trait plant of the invention, by genetic transformation techniques; and, such Nr:1 resistant plants that have additional genetic information introduced into the genome or that express additional traits by having the DNA coding therefor introduced into the genome via transformation techniques, are within the ambit of the invention, as well as uses of such plants, and the making of such plants.

Genetic transformation may therefore be used to insert a selected transgene into the plant of the invention or may, alternatively, be used for the preparation of transgenes which can be introduced by backcrossing. Methods for the transformation of plants are well known to those of skill in the art.

Vectors used for the transformation of cells are not limited so long as the vector can express an inserted DNA in the cells. For example, vectors comprising promoters for constitutive gene expression in cells (e.g., cauliflower mosaic virus 35S promoter) and promoters inducible by exogenous stimuli can be used. Examples of suitable vectors include pBI binary vector. The cell" into which the vector is to be introduced includes various forms of cells, such as cultured cell suspensions, protoplasts, leaf sections, and callus. A vector can be introduced into cells by known methods, such as the polyethylene glycol method, polycation method, electroporation, *Agrobacterium*-mediated transfer, particle bombardment and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including Nr:1 resistance trait of the invention.

Agrobacterium-mediated transfer is another widely applicable system for introducing gene loci into plant cells. An advantage of the technique is that DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes can be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including plant cells, is well known in the art (See, e.g., U.S. Pat. Nos. 7,250,560 and 5,563,055).

Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from (psaD, psaF, psaE, PC, FNR, atpC, atpD, cab, rbcS) (see U.S. Pat. No. 7,161,061), the CAB-1 promoter from (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the Nr:1 resistance trait of this invention include, for example, DNA sequences or genes from another species, or even genes or sequences which originate with or are present in species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a Nr:1 resistance trait plant according to the invention. Non-limiting examples of particular genes and corresponding phenotypes one may choose to introduce into a plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above RELATED APPLICATIONS & INCORPORATION BY REFERENCE section, are additionally cited as examples of U.S. patents that may concern transformed and/or methods of transforming plants or plant cells, and techniques from these US patents, as well as promoters, vectors, etc., may be employed in the practice of this invention to introduce exogenous nucleic acid sequence(s) into the Nr:1 resistance plant (or cells thereof) of the invention, and exemplify some exogenous nucleic acid sequence(s) which can be introduced into the Nr:1 resistant plant (or cells thereof) of the invention, as well as techniques, promoters, vectors etc., to thereby obtain further Nr:1 resistance trait plants, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material comprises inter alia seeds of the claimed plant and parts of the plant that are suitable for sexual reproduction. Such parts are for example selected from the group consisting of seeds, microspores, pollen, ovaries, ovules, embryo sacs and egg cells. In addition, the invention relates to propagation material comprising parts of the plant that are suitable for vegetative reproduction, for example cuttings, roots, stems, cells, protoplasts.

According to a further aspect thereof the propagation material of the invention comprises a tissue culture of the claimed plant. The tissue culture comprises regenerable cells. Such tissue culture can be derived from leaves, pollen, embryos, cotyledon, hypocotyls, meristematic cells, roots, root tips, anthers, flowers, seeds and stems. (See generally U.S. Pat. No. 7,041,876 on being recognized as a plant that can be regenerated from cultured cells or tissue).

According to another aspect of the invention plants are provided that have all of the morphological and physiological characteristics corresponding to the Nr:1 resistance trait of Nr:1 resistant plants of the invention, representative seed of which having been deposited under NCIMB Accession No NCIMB 41763, which plants are grown from seeds of a plant of the invention or regenerated from parts thereof, or from a tissue culture. Plants of the invention should have the morphological and physiological characteristics that correspond with the Nr:1 resistance trait but do not necessarily have all the other characteristics of plants of the deposited seeds. The trait is broadly transferrable over multiple types and varieties.

The invention further relates to cells of Nr:1 resistant plants as described herein. The cells comprise the genetic information that leads to the Nr:1 resistance trait as described herein. Suitably, this genetic information is substantially identical, preferably completely identical to the genetic information encoding the Nr:1 resistance trait of plants that have all of the morphological and physiological characteristics pertaining to the Nr:1 resistance trait of Nr:1 resistant plants of the invention, representative seed of which having been deposited under accession number NCIMB 41763. Preferably, the cell of the invention is part of a plant or plant part, but the cell may also be in isolated form.

In an embodiment the plants of the invention are plants grown from seeds having the deposit accession number NCIMB 41763.

In an embodiment the plants of the invention are progeny plants of plants grown from seeds having the deposit accession number NCIMB 41763 that carry the Nr:1 resistance trait.

In an embodiment the plants of the invention are plants that carry in their genome the genetic information that is responsible for the Nr:1 resistance trait by causing the plant to form significantly more leaves than a plant not having the said genetic information in its genome.

The invention, furthermore, relates to hybrid seed and to a method of producing hybrid seed comprising crossing a first parent plant with a second parent plant and harvesting the resultant hybrid seed. In order for the hybrid seed to express the trait of the invention, both parent plants need to be homozygous for the Nr:1 resistance trait but not necessarily uniform for other traits.

The invention also relates to the germplasm of plants of the invention. The germplasm is constituted by all inherited characteristics of an organism and according to the invention encompasses at least the Nr:1 resistance trait of the invention.

The invention also relates to the Nr:1 resistant leaves that are produced by the plants of the invention and marketed as vegetables, either as fresh vegetables or processed, i.e. cooked, and optionally frozen.

The invention further relates to a container comprising one or more plants of the invention in a growth substrate for harvest of leaves from the plant in a domestic environment. This way the consumer can pick very fresh leaves for use in salads. More generally, the invention includes one or more plants of the invention wherein the plant is in a ready-to-harvest condition, including with the consumer picking his own, and further including a container comprising one or more of these plants.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLE

Protocol of the Young-Plant Test

In order to test whether a plant is resistant to Nr:1 the following test is performed.

Seeds are sown in potting compost blocks. Twenty plants per line were evaluated. The young plants are inoculated 2 weeks after sowing by pouring aphids of the Nr:1 biotype on the top of the plants. One week after inoculation, the test is scored. The second and final score occurs two weeks after inoculation.

Nasonovia ribisnigri Isolates

The Nr:1 isolate used in this example was sampled in 2007 from Koningen (Germany) on a Nr:0 resistant variety Estelle (Nunhems): sample 279. The aphid isolate is maintained on the variety Kitare (Nr:0 resistant variety, Rijk Zwaan).

Introduction of the Nr:1 Resistance into Susceptible Lettuce

A cross between a susceptible lettuce variety *L. sativa* used as a female and *L. serriola* used a male was performed. The F1 seeds were sown and the F2 generation was obtained. After this, 150 F2 seeds were sown and propagated to generate 150 F3 lines. From these, 100 F3 lines were included in Nr:0 and Nr:1 tests.

The F3 line 09D.857022 was found resistant in 2008 (in test 08D.846) and the results were confirmed in 2009 (in test 09D.846). From the test 08D.846, 3 resistant plants were selected. This F3 line was also tested against Nr:0 twice and this line displayed a susceptible reaction. The 3 F4 lines resulting from the 3 resistant F3 plants (09D.861266, 09D.861267 and 09D.861268) were then tested against Nr:1 in test 09D.841 and the 3 lines displayed a resistant behaviour. From 09D.861266, 4 F5 plants were selected. Those 4 F5 lines (09D.873417, 09D.873418, 09D.873419 and 09D.873420) were then included in test 09D.846 and all of them displayed a resistant reaction. From line 09D.874317, 10 plants were selected from this test. The 10 F6 lines were tested in 10D.831 and all the lines were detected resistant. The 10 lines were bulked to obtain a seed lot for a seed deposit, 10G.913569.

Nr:1 resistant *L. sativa* 10G.913569 plants (called herein "the donors") were used to introgress the Nr:1 resistance into susceptible lettuce varieties.

The donors were crossed to a cultivated susceptible lettuce variety. Cultivated varieties belonging to different lettuce types were used. The F1s obtained were selfed. Then, the different F2 populations were placed in a Nr:1 disease resistance test as described above. At the end of the test, Nr:1 resistant plants were selected for further development.

The invention is further described by the following numbered paragraphs:

1. A lettuce plant (*Lactuca sativa* L.) resistant against *Nasonovia ribisingi* biotype 1 (Nr:1) representative seeds of which were deposited under NCIMB accession number 41763.

2. Lettuce plant of paragraph 1, obtainable by crossing a lettuce plant with a plant grown from seeds of seedlot 10G.913569 representative seeds of which were deposited with the NCIMB under NCIMB accession number 41763 and selecting preferably in the F2 progeny of the cross for plants being resistant against *Nasonovia ribisingi* biotype 1 (Nr:1).

3. Lettuce plant of paragraph 1 or 2, being resistant against Nr:1 as compared to a susceptible control plant, and which plant is obtainable by crossing a lettuce plant with a plant grown from seeds of lettuce plant 10G.913569 representative seeds of which were deposited with the NCIMB under NCIMB accession number 41763 and selecting in the F2 progeny of the cross that is obtained after selfing the F1 for plants being resistant against Nr:1.

4. Seed of a lettuce plant of any one of the paragraphs 1-3.

5. Progeny of a plant or seed of any of the paragraphs 1-4, which is resistant against Nr:1.

6. Propagation material of a plant of any one of the paragraphs 1 to 5, suitable for sexual reproduction, in particular microspores, pollen, ovaries, ovules, embryo sacs and egg cells.

7. Plant parts of a plant of any one of the paragraphs 1 to 5, suitable for vegetative reproduction, in particular cuttings, roots, stems, cells, protoplasts, and tissue culture.

8. Head of a lettuce plant of any one of the paragraphs 1-5.

9. Food product, comprising the lettuce head of paragraph 8 or parts thereof.

10. Food product of paragraph 8, wherein the parts are leaves or parts thereof.

11. Use of *Lactuca sativa* 10G.913569, representative seeds of which were deposited under NCIMB accession number 41763, in breeding to confer resistance against *Nasonovia ribisnigri* biotype 1 (Nr:1) to plants that are susceptible to *Nasonovia ribisnigri* biotype 1 (Nr:1).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A lettuce plant (*Lactuca sativa* L.) resistant against *Nasonovia ribisnigri* biotype 1 (Nr:1), wherein the resistance is as found in plants grown from seeds of which a representative sample was deposited under NCIMB accession number 41763.

2. The lettuce plant as claimed in claim 1, wherein the plant is resistant against *Nasonovia ribisnigri* biotype 1 (Nr:1), representative seeds of which were deposited under NCIMB accession number 41763.

3. A seed of a lettuce plant as claimed in claim 1.

4. A progeny of a plant as claimed in claim 1, wherein the progeny is resistant against Nr:1, wherein the resistance of the progeny is as found in plants grown from seeds of which a representative sample was deposited under NCIMB accession number 41763.

5. A propagation material of a plant as claimed in claim 1 suitable for sexual reproduction, wherein the propagation material is a microspore, pollen, ovary, ovule, embryo sac or egg cell.

6. A part of a plant as claimed in claim 1 suitable for vegetative reproduction, wherein the part is a cutting, root, stem, cell, protoplast or tissue culture.

7. A head of the lettuce plant as claimed in claim 1.

8. A food product, comprising the head of claim 7 or a part thereof.

9. The food product as claimed in claim 8, wherein the part is a leaf or a part thereof.

* * * * *